United States Patent
Lin et al.

(10) Patent No.: US 11,915,386 B2
(45) Date of Patent: Feb. 27, 2024

(54) HIGH-THROUGHPUT MICROSTRUCTURE CHARACTERIZATION AND RECONSTRUCTION METHOD OF HETEROGENEOUS MATERIALS

(71) Applicant: DALIAN UNIVERSITY OF TECHNOLOGY, Liaoning (CN)

(72) Inventors: Li Lin, Liaoning (CN); Zhiyuan Ma, Liaoning (CN); Yijia Chen, Liaoning (CN); Luoming Sun, Liaoning (CN); Xiyu Xie, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 18/262,192

(22) PCT Filed: Nov. 25, 2022

(86) PCT No.: PCT/CN2022/134206
§ 371 (c)(1),
(2) Date: Jul. 19, 2023

(87) PCT Pub. No.: WO2023/134310
PCT Pub. Date: Jul. 20, 2023

(65) Prior Publication Data
US 2024/0037699 A1    Feb. 1, 2024

(30) Foreign Application Priority Data

Jan. 11, 2022  (CN) .......................... 202210029135.5
Apr. 25, 2022  (CN) .......................... 202210440960.4

(51) Int. Cl.
*G06T 7/00*  (2017.01)
*G06T 3/40*  (2006.01)
*G06T 7/136*  (2017.01)

(52) U.S. Cl.
CPC ................ *G06T 3/40* (2013.01); *G06T 7/136* (2017.01); *G06T 2207/10056* (2013.01); *G06T 2207/20016* (2013.01); *G06T 2207/30108* (2013.01)

(58) Field of Classification Search
CPC . G06T 3/40; G06T 7/136; G06T 2207/10056; G06T 2207/20016; G06T 2207/30108
See application file for complete search history.

(56) References Cited

U.S. PATENT DOCUMENTS

| | | | |
|---|---|---|---|
| 2006/0241920 | A1 | 10/2006 | Le Ravalec-Dupin et al. |
| 2015/0057988 | A1 | 2/2015 | Yun |
| 2022/0392078 | A1* | 12/2022 | Bolintineanu .......... G06T 7/136 |

FOREIGN PATENT DOCUMENTS

| | | |
|---|---|---|
| CN | 105139444 A | 12/2015 |
| CN | 107204042 A | 9/2017 |

(Continued)

OTHER PUBLICATIONS

Bostanabad, Ramin, et al. "Computational microstructure characterization and reconstruction: Review of the state-of-the-art techniques." Progress in Materials Science 95 (2018): 1-41. (Year: 2018).*

(Continued)

*Primary Examiner* — Li Liu
(74) *Attorney, Agent, or Firm* — NKL Law; Allen Xue

(57) ABSTRACT

A high-throughput microstructure characterization and reconstruction method of heterogeneous materials is provided. By extracting the features such as content, size and morphology of each constituent phase in the microscopic image of heterogeneous materials, and combining the principles of physical descriptor and texture synthesis method, the constituent phase with 10 microns scale, regular geometrical morphology and low content is characterized and reconstructed based on the physical descriptor, and the constituent phase with 100 microns scale, complex geometrical morphology and high content is characterized and reconstructed based on texture synthesis, and then the composition is adjusted to compensate for the overlapping pixels (Continued)

of each constituent phase to obtain batch reconstructed images.

1 Claim, 7 Drawing Sheets

(56) References Cited

FOREIGN PATENT DOCUMENTS

| CN | 108648256 A | 10/2018 |
|---|---|---|
| CN | 108765554 A | 11/2018 |
| CN | 112632661 A | 4/2021 |
| CN | 114820312 A | 7/2022 |

OTHER PUBLICATIONS

Li, Lin, et al. "Random multi-phase medium model and its application in analysis of ultrasonic propagation characteristics for AlSi-polyester abradable seal coating." NDT & E International 108 (2019): 102173. (Year: 2019).*

Senthilnathan, Arulmurugan, Pinar Acar, and Marc De Graef. "Markov Random Field based microstructure reconstruction using the principal image moments." Materials Characterization 178 (2021): 111281. (Year: 2021).*

Fu, Yu et al.; "Heterogeneous Characteristics of coal based on CT scanning and numerical analysis of its reconstruction model"; Journal of Mining & Safety Engineering; vol. 37, No. 4; Jul. 2020; pp. 828-835.

* cited by examiner

HIGH-THROUGHPUT MICROSTRUCTURE CHARACTERIZATION AND RECONSTRUCTION METHOD OF HETEROGENEOUS MATERIALS

TECHNICAL FIELD

The present invention relates to a high-throughput microstructure characterization and reconstruction method of heterogeneous materials, belonging to the field of material microstructure characterization and reconstruction.

BACKGROUND

Heterogeneous materials are widely used in aerospace, biology, energy and other fields, which may meet the high comprehensive performance requirements including heat insulation, wear resistance, wave absorption, sealing relying on the synergistic effect of different constituent phases in the material. Microstructure features of heterogeneous materials have a very important impact on their macroscopic properties and quality control. Currently, most studies on the microstructure of heterogeneous materials are based on advanced experimental imaging technology, such as metallographic microscopic observation, scanning electron microscopy, CT imaging, nuclear magnetic resonance imaging, etc.

Among them, destructive metallographic microscopic observation is a relatively mature characterization technology of material microstructure at present. In order to obtain microstructure information of different parts of a sample, the sample is usually gradually thinned by slicing method, so as to obtain a large number of microscopic images. The local statistical result of the microstructure obtained by this traditional experimental method is accurate, but the experimental process is time-consuming, laborious and inefficient, and it is difficult for the local observation result to represent the structural features of each part of the material. With the development of imaging instruments, CT imaging, nuclear magnetic resonance imaging and other technologies avoid the time-consuming and low efficiency of destructive slicing method, which are gradually used in the study of material microstructure. However, limited to the cost of experimental instrument, imaging resolution and sample size, it often requires a relatively high number of samples and equipment resources, and is greatly affected by the technical level and experience status of observer, making it difficult to obtain detailed material microstructure features, which limits its widespread application.

Compared to the above experimental imaging methods, material microstructure characterization and reconstruction (MCR) technology can generate a large number of equivalent models in a few or a single microscopic image by means of a computational method. This high-throughput computational method avoids consuming a large amount of experimental data and can effectively characterize the microstructure by using representative reconstruction models. MCR methods mainly include correlation function, random field, physical descriptor, texture synthesis, etc., which have been applied to the microstructure characterization and reconstruction of some two-phase, single-scale and simple structure materials. However, heterogeneous materials have the features of multi-phase, multi-scale, complex morphology, etc., which makes the above various MCR methods have great technical difficulties.

The physical descriptor method can retain the physical significance such as particle size, content, aspect ratio and the like, and is suitable for reconstruction of two-phase regular structure at the scale of 10 microns or below. When heterogeneous materials contain three-phase or multi-phase structures, it will cause a more complex micro-morphology, making it difficult to extract physical descriptors, resulting in reconstruction results diverting from the real morphology and poor universality. The texture synthesis method can capture the complex morphological features in the microstructure, and has great advantages for large-scale phase reconstruction with the scale of 100 microns. When the scale span between different phases in multi-phase heterogeneous materials is large, it is easy to ignore the randomly distributed small-scale phases, resulting in a large error of reconstruction. At present, there is no MCR method capable of demonstrating the comprehensive features of multi-phase, multi-scale and complex morphology of heterogeneous materials.

With regard to the abovementioned problems, the present invention comprehensively considers the limitations and applicability of two methods of physical descriptor and texture synthesis, and proposes a two-dimensional MCR method suitable for heterogeneous materials with multi-phase, multi-scale and complex morphology. This method can, by means of high-throughput characterization and reconstruction, fuse the advantages of physical descriptor in reconstructing geometric morphology with regular phases at the 10 micron scale, as well as the advantages of texture synthesis in reconstructing geometric morphology with complex phases at the 100 micron scale, improving the accuracy of microstructure characterization and reconstruction of heterogeneous materials.

SUMMARY OF THE INVENTION

Aiming at the problems that traditional experimental methods require a large amount of sample data and equipment resources, as well as the significant technical difficulties of the MCR of heterogeneous materials, the present invention provides a high-throughput microstructure characterization and reconstruction method of heterogeneous materials, combining the principles of physical descriptor and texture synthesis. By using the physical descriptor to extract the size, content, aspect ratio, and other physical significances of particles with 10 microns scale and the theory of multi-resolution synthesis and neighborhood search for texture synthesis of complex phases with 100 micros scale, the present invention realizes batch characterization and reconstruction of heterogeneous materials with multi-phase, multi-scale and complex morphology, provides an effective approach for MCR of heterogeneous materials, and has good popularization and application value.

Technical solutions adopted by the present invention to solve the technical problems are as follows: a high-throughput microstructure characterization and reconstruction method of heterogeneous materials mainly includes four parts of feature characterization, structure reconstruction, feature optimization and composition adjustment of a microscopic image, and using the following steps of:

1) Observing a Microscopic Image of a Sample

Divide the heterogeneous sample into small pieces by a wire cut electrical discharge machining technology, grind the sample cross-section with water abrasive paper, followed by polishing and ultrasonic cleaning, and use microscopic observation technology to image the microscopic morphology of the sample cross-section to obtain the original microscopic image $I_s$ of the sample.

2) Extracting Microstructure Features of Each Constituent Phase

Thresholding process the original microscopic image $I_s$ including the matrix phase, the constituent phase A and the constituent phase B to separate $I_s$ into binary images of the matrix phase and each constituent phase, that is, separate the sample image $I_s$ including n constituent phases A and m constituent phases B into binary images of "matrix phase+phase $A_1$", "matrix phase+phase $A_2$" . . . "matrix phase+phase $A_k$" . . . "matrix phase+phase $A_n$", "matrix phase+phase $B_1$", "matrix phase+phase $B_2$" . . . "matrix phase+phase $B_j$" . . . "matrix phase+phase $B_n$", wherein, A represents the constituent phase with a size not larger than 10 microns in the original microscopic image $I_s$, B represents the constituent phase with a size not less than 100 microns in the original microscopic image $I_s$, $A_k$ represents the in the $k^{th}$ (k=1, 2, . . . , n) constituent phase with a size not larger than 10 microns in the original microscopic image $I_s$, and $B_j$ represents the $j^{th}$ (j=1, 2, . . . , m) constituent phase with a size not less than 100 microns in the original microscopic image $I_s$.

Extract five physical descriptors of the nearest neighbor distance d, number N, area S, aspect ratio $\alpha$ and volume fraction VF of all particles in the binary image of each constituent phase A;

$$S_i = q_i (i = 1, 2, \ldots, N) \quad (1)$$

$$\alpha_i = \frac{a_1}{b_1}(i = 1, 2, \ldots, N) \quad (2)$$

wherein, $q_i$ represents an area of a pixel region occupied by the $i^{th}$ particle in the $k^{th}$ constituent phase, $a_i$ and $b_i$ represent lengths of the short axis and the long axis of the $i^{th}$ particle in the $k^{th}$ constituent phase, respectively;

$$VF = \frac{\sum_{i=1}^{N} S_i}{M \times H} \quad (3)$$

wherein, M×H represents an area of the microscopic image, which is usually expressed by the total number of pixels of the digitally processed image.

3) Constructing a multi-resolution pyramid of the constituent phase $B_j$

Construct an L-layer multi-resolution pyramid of the binary images of "matrix phase+constituent phase $B_j$", L can usually be selected a value ≥3 according to the resolution of the original microscopic image, obtain a sample pyramid image $X_j^l$ (l=1, 2, . . . , L) with a resolution from high to low, and construct an L-layer pyramid $Y_j^l$ (l=1, 2, . . . , L) of $B_j'$ to-be-generated.

4) Constructing a set of neighborhood pixels of the constituent phase $B_j$

For each pixel point t to-be-output, take t point as a center and express a neighborhood with a size of (2ω+1) as:

$$N_t = \{s : |t-s|_\infty \leq \omega, s \neq t\} \quad (4)$$

wherein, s represents the pixel points around the central pixel point t, and ω represents a size of the neighborhood.

Search pixel by pixel according to raster scanning order, and learn the neighborhood distribution in $X_j^{L-h}$ (h=1, 2 . . . , L−1) and $Y_j^l$ (l=1, 2 . . . L), an entire neighborhood set $N_P$ at this time including neighborhood pixels of the current layer $X_j^{L-k}$ and neighborhood pixels of the synthesized previous layer $Y_j^L$.

5) Reconstructing the constituent phase $B_j$ according to texture synthesis

For inputting a known sample $B_j$, the goal of texture synthesis is to output a new $B_j$ so that the pixel distribution features in each neighborhood match the input image best, according to the multi-resolution synthesis and the neighborhood search theory in steps 3) and 4), gradually synthesize a microscopic image $Y_j^L$ equivalent to $X_j^L$ from the lowest resolution level, and obtain a final reconstructed image $Y_j^l$ by stacking resolution images layer-by-layer to the highest resolution layer, that is, the reconstructed result $B_j'$ of constituent phase $B_j$.

6) Adjusting the composition of the constituent phase B

Repeat steps 3) to 5), superimpose the matrix phase and the reconstructed results of each constituent phases $B_j'$ to obtain the base image B' of all constituent phases B, identify edges of all particles in B', and increase or decrease pixels at edges of particles in the non-overlapping part, so as to ensure that the volume fraction of B' is consistent with that of the constituent phase B in the original microscopic image $I_s$.

7) Constructing dispersion of the constituent phase $A_k$

On the synthesized base image B', randomly generate centroid positions according to the particles number N in the constituent phase $A_k$ extracted in step 2) to obtain an initialized microstructure, take the centroid position distribution of the particles in the initialized microstructure and the centroid position distribution of the particles in the binary image of the sample $A_k$ as the systems under high temperature and zero Kelvin respectively, set initial parameters of the simulated annealing algorithm, randomly exchange centroid positions of the particles, and calculate a deviation between the nearest neighbor distance of the particles after exchange and the sample $A_k$ and a deviation between that before exchange and the sample $A_k$; if the deviation decreases, accept the exchange, otherwise, calculate a probability of accepting an exchange according to the Metropolis rule:

$$P = \begin{cases} 1 & \Delta E \leq 0 \\ e^{-\frac{\Delta E}{T(k)}} & \Delta E > 0 \end{cases} \quad (5)$$

wherein, T(k) represents a temperature of the current iteration step, and $\Delta E$ represents an energy change of the system.

Gradually lower the temperature and continue to exchange the centroid positions, terminate the iteration until the deviation of the nearest neighbor distance d is less than 6, and obtain the distribution state of the centroid of particles in the constituent phase $A_k$.

8) Reconstructing the constituent phase $A_k$ according to the physical descriptors Generate the shape and size of each cluster according to the area S and the aspect ratio $\alpha$ of all particles in the constituent phase $A_k$ extracted in step 2), and add each cluster to the centroid position of the particles obtained in step 7) to obtain a reconstructed result $A_k'$ of $A_k$.

9) Adjusting composition

For the problem of pixel overlapping generated by a fusion of $A_k'$ and B', identify the edges of all particles in the $A_k'$ and B', and increase or decrease pixels at the edges of particles in the non-overlapping part to adjust the composition until the volume fractions VF of $A_k'$ and B' are consistent with that of the constituent phase $A_k$ and B in the sample image $I_s$, so as to ensure the accuracy of the volume fraction of each constituent phase.

10) Repeat steps 7)-9) to reconstruct all the constituent phases A on the base image to obtain a final reconstructed image $I_c$ of $I_s$.

The effect and benefit of the present invention are as follows:

A high-throughput microstructure characterization and reconstruction method of heterogeneous materials, which solves the problems of time-consuming and inefficient characterization of material microstructure affected by factors such as resolution of instrument imaging, sample size, and technical level of observers in traditional experimental methods. The present method combines the principles of physical descriptor and texture synthesis, taking into account the advantages of physical descriptor in reconstructing small-scale phase physical meanings and texture synthesis in reconstructing large-scale phase complex morphology, which can provide an effective approach for characterizing and reconstructing the microstructure of heterogeneous materials with multi-phase, multi-scale and complex morphology, and has good promotion and application value.

DETAILED DESCRIPTION OF DRAWINGS

DETAILED DESCRIPTION OF PREFERRED EMBODIMENTS

The method provided in the present invention realizes high-throughput microstructure characterization and reconstruction of materials based on the four main parts of feature characterization, structure reconstruction, feature optimization, and composition adjustment of a microscopic image. The experimental sample in one embodiment was a plasma sprayed aluminum-silicon polyester (AlSi-PHB) seal coating sample, using the following reconstruction steps:

1) Observation of the microscopic image of the seal coating sample

Figure 1:
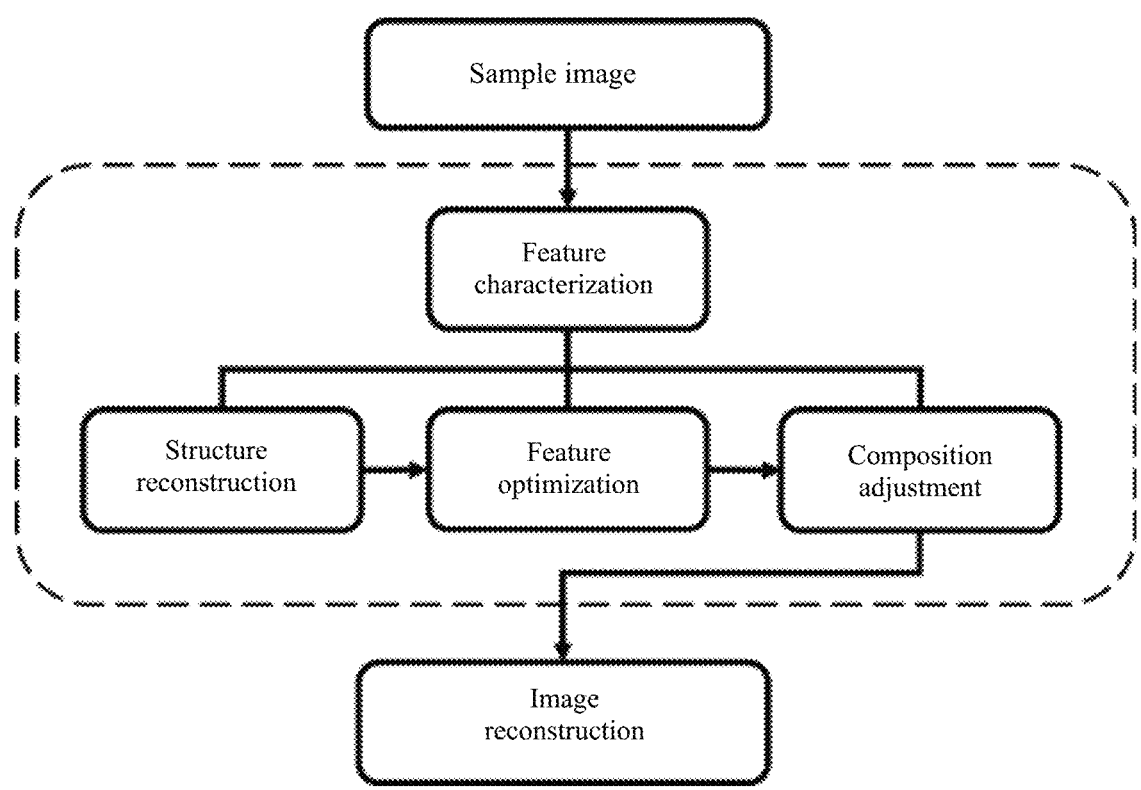
FIG. 1 shows a schematic diagram of the microstructure characterization and reconstruction method of heterogeneous materials.
Figure 2:
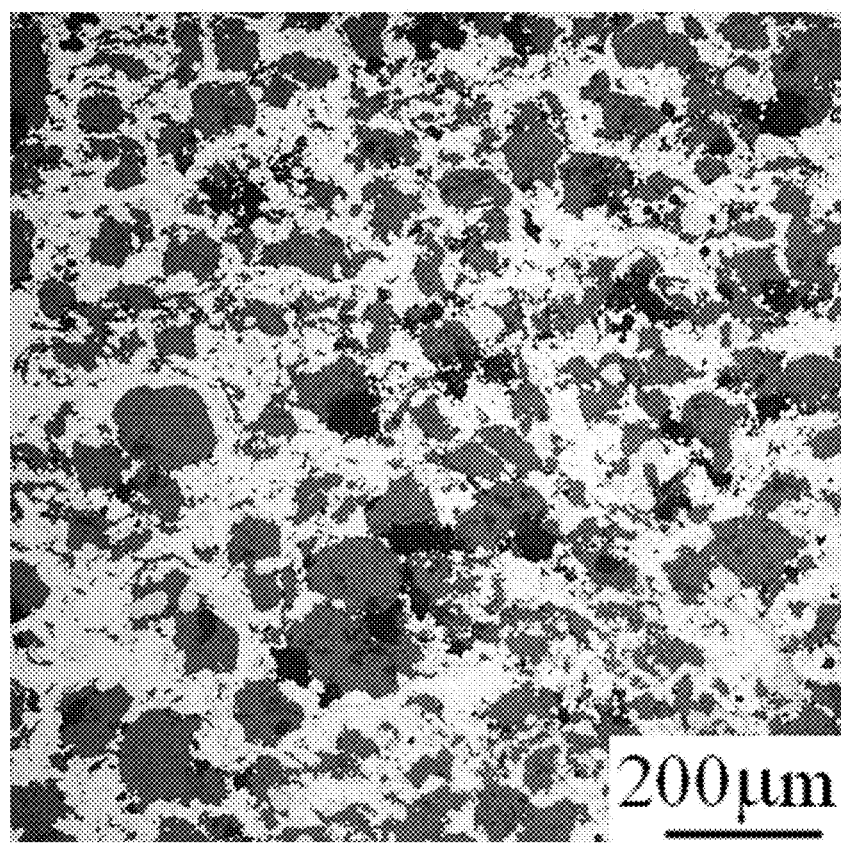
FIG. 2 shows an original microscopic image of a seal coating sample.

A heterogeneous sample is divided into small pieces by a wire cut electrical discharge machining technology, and the sample cross-section is ground with water abrasive paper, and followed by polishing and ultrasonic cleaning. Microscopic observation technology is used to image the microscopic morphology of the sample cross-section. As shown in FIG. 2, the original microscopic image $I_s$ of the seal coating containing three-phase microstructure of aluminum-silicon matrix, polyester and pores was obtained.

2) Extraction of microstructure features of each constituent phase

Figure 3:
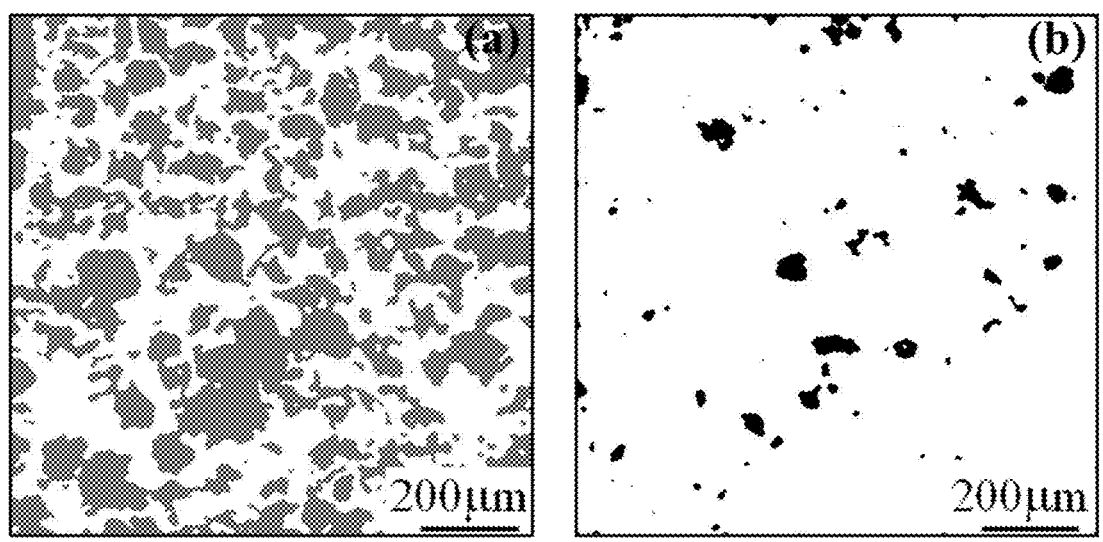
FIG. 3 shows binary image of each constituent phase of the original microscopic image after thresholding processing.
Figure 4:
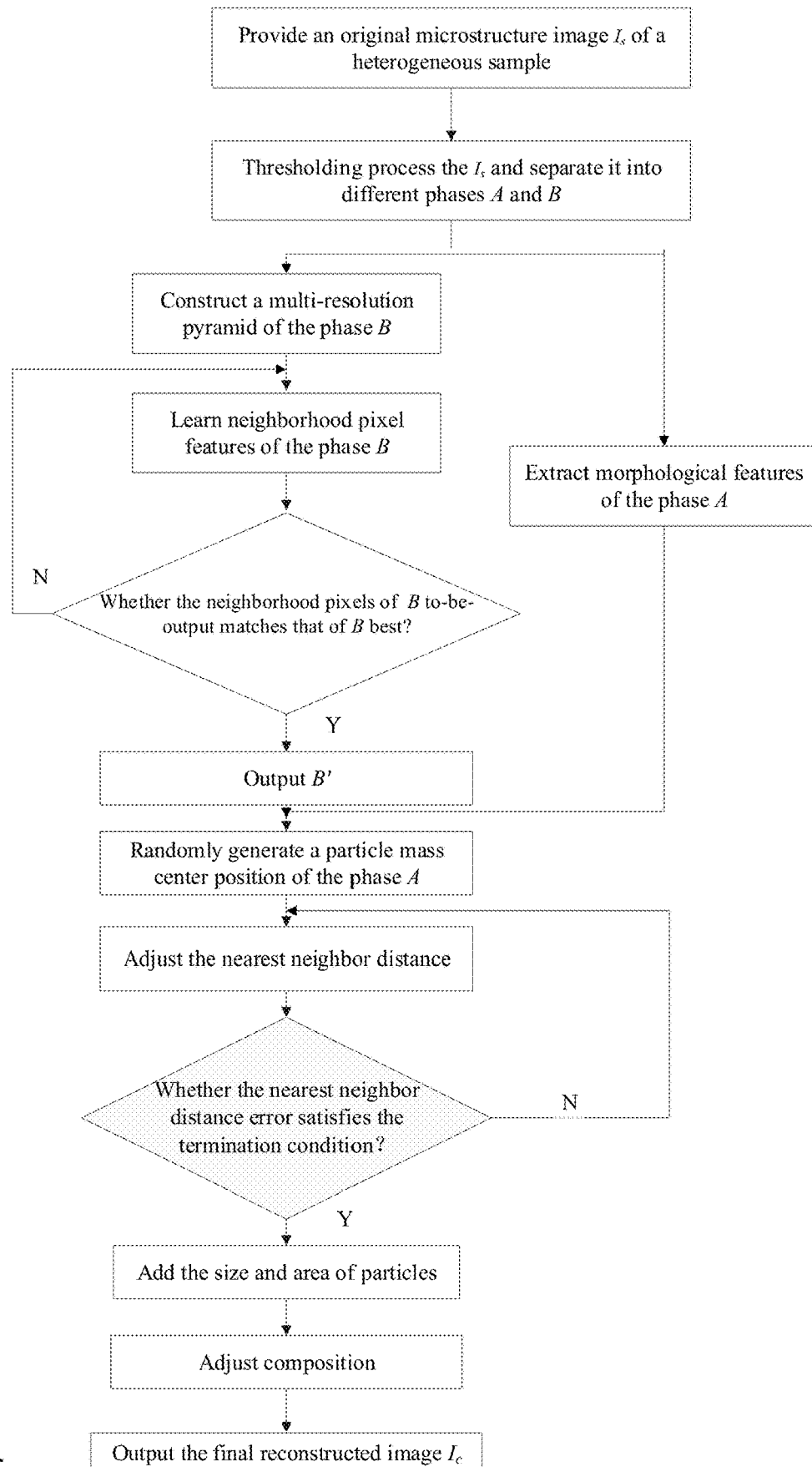
FIG. 4 shows a flow chart of characterization and reconstruction method for a two-dimensional microstructure of the seal coating sample.

The original microscopic image $I_s$ is thresholding processed. As shown in FIG. 3, $I_s$ was separated into binary images of "AlSi matrix+pore phase $A_1$" and "AlSi matrix+polyester $B_1$" by thresholding processing, where the size distribution of the pore ranges from about 0 μm-40 μm and the content of that is less than 4%, and the size distribution of polyester ranges from about 40 μm-400 μm and the content of that ranges from about 40%-50%.

Five physical descriptors of the nearest neighbor distance d, number N, area S, aspect ratio α and volume fraction VF of all particles in the pore phase $A_1$ are extracted, $$S_i = q_i (i = 1, 2, \ldots, N) \quad (1)$$

$$\alpha_i = \frac{a_1}{b_1} (i = 1, 2, \ldots, N) \quad (2)$$

where $q_i$ represents an area of the pixel region occupied by the $i^{th}$ pore, and $a_i$ and $b_i$ represent lengths of the short axis and the long axis of the $i^{th}$ pore, respectively;

$$VF = \frac{\sum_{i=1}^{N} S_i}{M \times H} \quad (3)$$

where M×H represents an area of the microscopic image, which is usually expressed by the total number of pixels of the digitally processed image.

3) Construction of the multi-resolution pyramid of the polyester phase $B_1$

An L-layer multi-resolution pyramid of "AlSi matrix+polyester phase $B_1$" is constructed, and a sample pyramid image $X_j^l$ (l=1, 2, . . . , L) with a resolution from high to low was obtained, and an L-layer pyramid $Y_j^l$ (l=1, 2, . . . , L) of $B_1$' to-be-generated was constructed.

In the embodiment, L=4 was taken according to the resolution of the original microscopic image.

4) Construction of a set of neighborhood pixels of the polyester phase $B_1$

For each pixel point t to-be-output, t point is taken as a center, and a neighborhood with a size of (2ω+1) can be expressed as:

$$N_t = \{s : \|t-s\|_\infty \leq \omega, s \neq t\} \quad (4)$$

where s represents the pixel points around the central pixel point t and ω represents a size of the neighborhood, and the selection of the neighborhood size should be generally greater than the maximum size of the polyester phase in the original image.

Search pixel by pixel according to raster scanning order, and learn the neighborhood distribution in $X^{L-h}_j$ (k=1, 2 . . . , L−1) and $Y_j^l$, an entire neighborhood set $N_P$ at this time includes neighborhood pixels of the current layer of $X^{L-k}_j$ (k=1, 2 . . . , L−1) and neighborhood pixels of the synthesized previous layer of $Y^L_j$.

5) Reconstruction of the polyester phase $B_1$ according to texture synthesis

Figure 5:
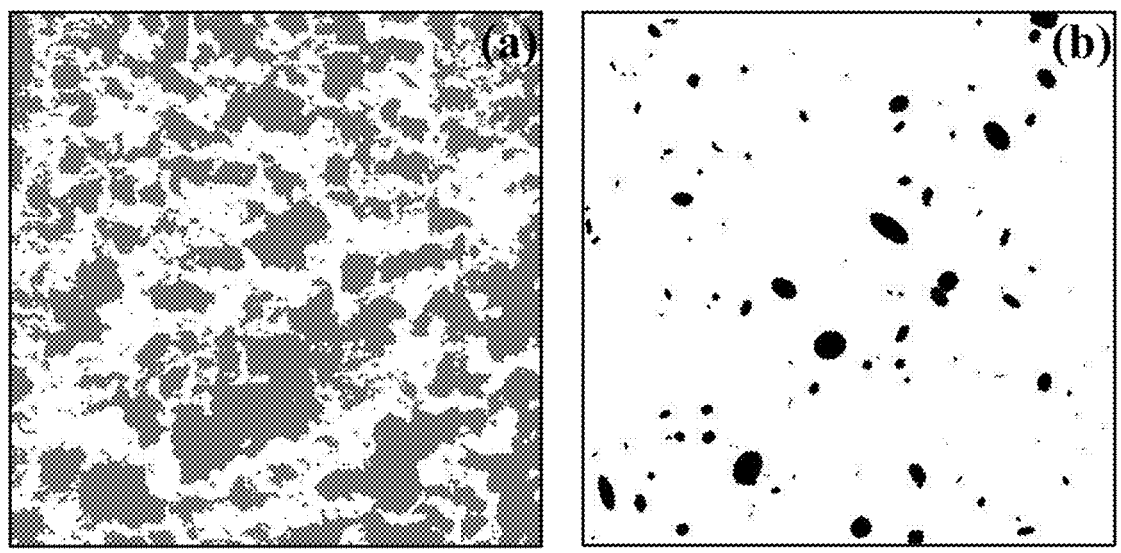
FIG. 5 shows a group of reconstructed result diagrams of the binary image of each constituent phase of the seal coating sample.

For inputting a known sample $B_1$, the goal of texture synthesis is to output a new $B_1$', so that the pixel distribution features in each neighborhood match the input image best. According to the multi-resolution synthesis and the neighborhood search theory in steps 3) and 4), a microscopic image $Y_j^L$ equivalent to $X_j^L$ is gradually synthesized from the lowest resolution level. As shown in FIG. 5, a final reconstructed image $Y_j^I$ by stacking the resolution images layer-by-layer to the highest resolution layer was obtained, that is, the reconstructed result $B_1'$ of $B_1$.

6) Adjustment of the composition of the polyester phase $B_1$

For the pixel overlapping problem between the reconstructed results $B_1'$, identify the edges of all particles in $B_1'$, and increase or decrease pixels at edges of particles in the non-overlapping part, ensuring that the volume fraction of $B_1'$ is consistent with that of the polyester phase $B_1$ in the sample microscopic image.

7) Construction of the dispersion of the pore phase $A_1$

On the synthesized base image $B_1'$, randomly generate centroid positions according to the particles number N in the pore phase $A_1$ extracted in step 2) to obtain an initialized microstructure. Take the centroid position distribution of the particles in the initialized microstructure and the centroid position distribution of the particles in the sample $A_1$ as the systems under high temperature and zero Kelvin respectively, set the initial parameters of the simulated annealing algorithm, randomly exchange centroid positions of the particles, and calculate a deviation between the nearest neighbor distance of the particles after exchange and the sample $A_k$ and a deviation between that before exchange and the sample $A_k$. If the deviation decreases, accept the exchange; otherwise, calculate a probability of accepting an exchange according to the Metropolis rule:

$$P = \begin{cases} 1 & \Delta E \leq 0 \\ e^{-\frac{\Delta E}{T(k)}} & \Delta E > 0 \end{cases} \quad (5)$$

where T(k) represents a temperature of the current iteration step and $\Delta E$ represents an energy change of the system.

Gradually lower the temperature and continue to exchange the centroid positions. The iteration is terminated until the deviation of the nearest neighbor distance d is less than 0.01, the distribution state of the centroid of particles in the pore phase $A_1$ is obtained.

8) Reconstruction of the pore phase $A_1$ according to physical descriptors

Generate the shape and size of each cluster according to the area S and the aspect ratio α of all particles in the pore phase $A_1$ extracted in step 2), and add each cluster to the centroid position of the particles obtained in step 7) to obtain the reconstructed result $A_1'$ of $A_k$. As shown in FIG. 5, the reconstructed result of the embodiment was obtained.

9) Adjustment of composition

For the pixel overlapping problem generated by a fusion of the pore phase $A_1'$ and the polyester phase $B_1'$ in the reconstructed result, identify the edges of all particles in the $A_1'$ and $B_1'$, and increase or decrease the pixels at the edges of particles in the non-overlapping part to adjust the composition until the volume fractions VF of $A_1'$ and $B_1'$ are consistent with that of the $A_1$ and $B_1$ in the sample image $I_S$, so as to ensure the accuracy of the volume fraction of each constituent phase and obtain the final reconstructed image $I_c$ of $I_s$.

Figure 6:
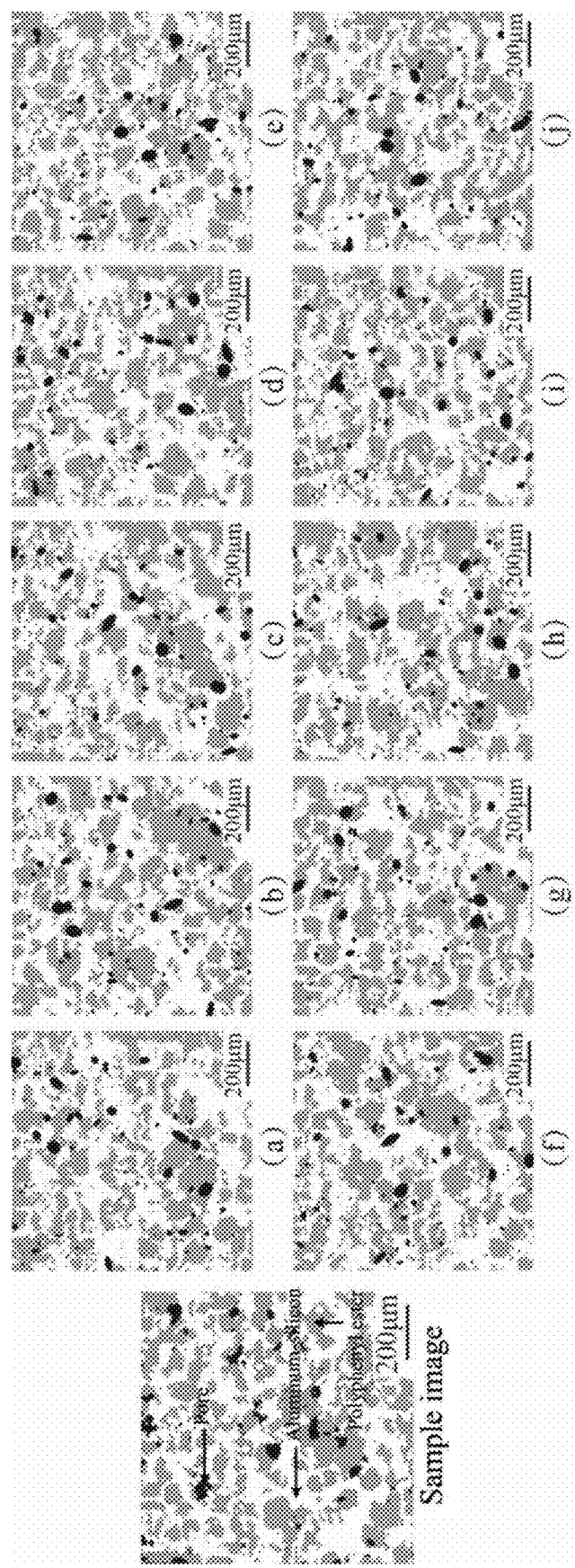
FIG. 6 shows a comparison of the microscopic morphology between the reconstructed image and the sample image.
Figure 7:
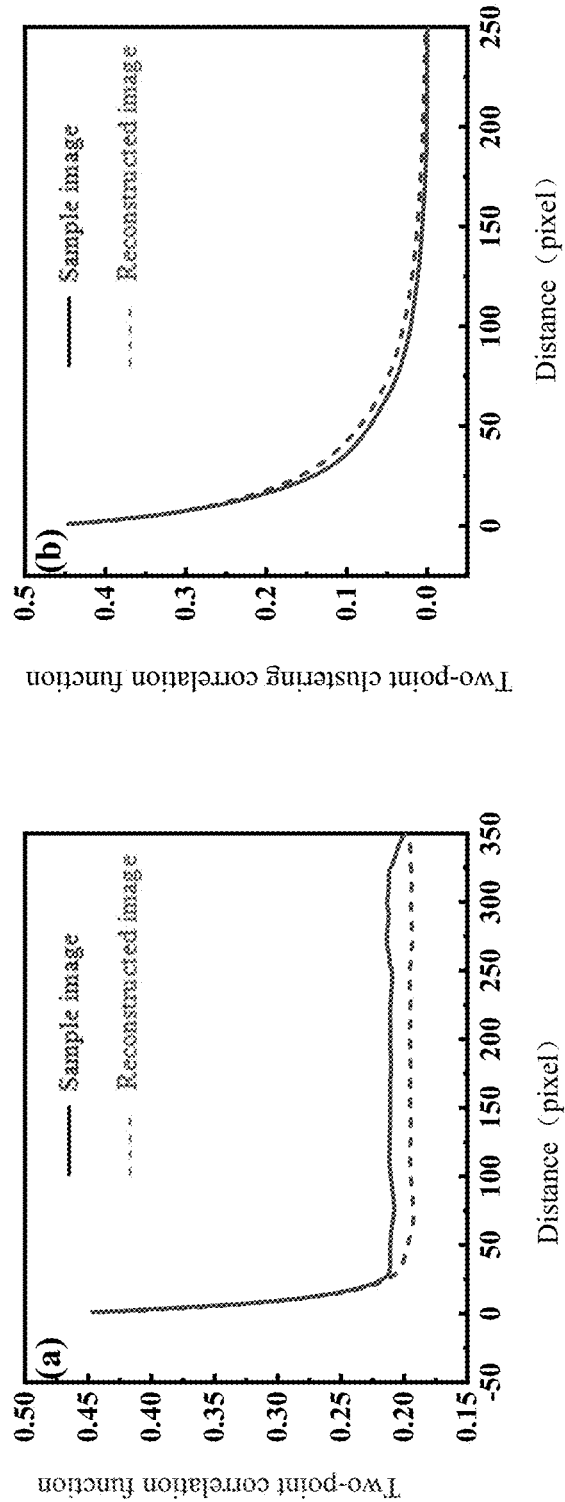
FIG. 7 shows a comparison of the correlation functions of the polyester in the reconstructed image and the sample image.
Figure 8:
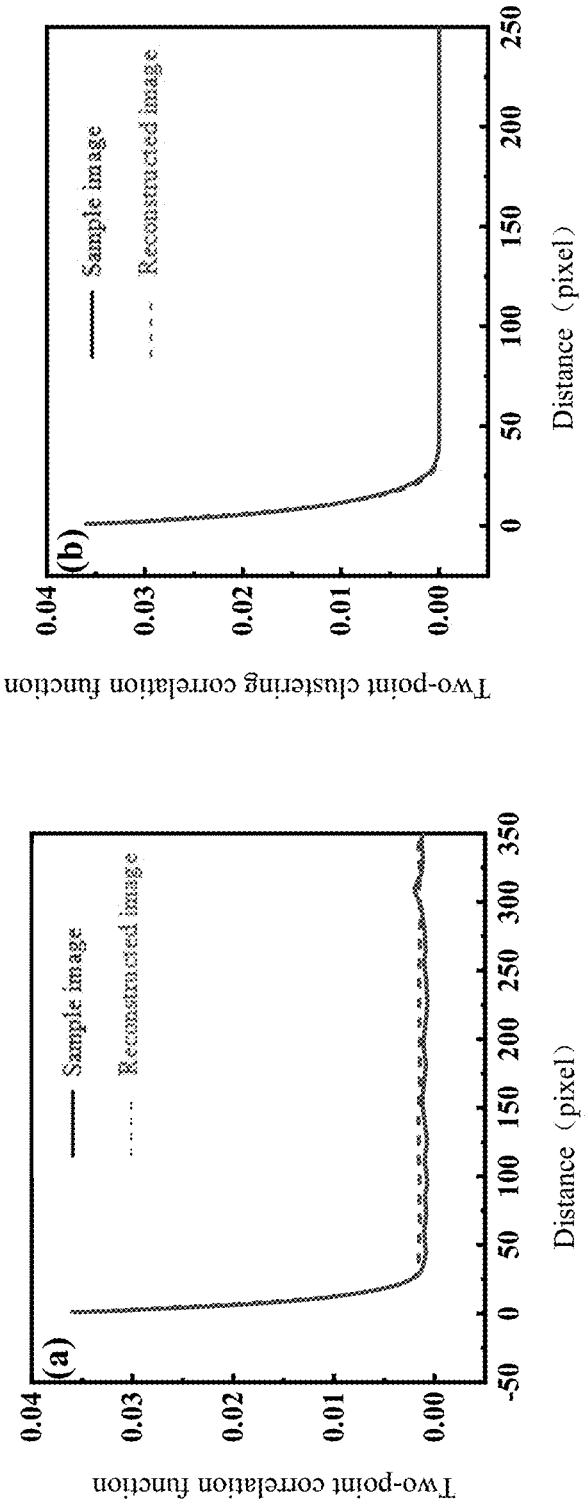
FIG. 8 shows a comparison of the correlation functions for the pores in the reconstructed image and the sample image.

In the embodiment, steps 2)-9) were repeated to obtain 10 groups of reconstructed images of seal coating samples, as shown in FIG. 6, indicating a good reconstruction effect; and the statistical characteristics of the pores and polyester in the reconstructed images and sample image were calculated by correlation function, verifying the equivalence of statistical significance of the reconstructed images and sample image. The correlation function features of the reconstructed images and the sample image are shown in FIGS. 7 and 8, showing a good consistency between the two.

The invention claimed is:

1. A high-throughput microstructure characterization and reconstruction method of heterogeneous materials, comprising four parts of feature characterization, structure reconstruction, feature optimization and composition adjustment of a microscopic image, and using the following steps of:

1) Observing a microscopic image of a sample performing microstructure morphology imaging on a cross-section of the sample by using microscopic observation technique to obtain an original microscopic image $I_s$ of the sample;

2) extracting microstructure features of each constituent phase thresholding processing the original microscopic image $I_s$ to separate it into binary images of a matrix phase and each constituent phase, wherein A represents a constituent phase with a size not larger than 10 microns in the original microscopic image $I_s$, B represents a constituent phase with a size not less than 100 microns in the original microscopic image $I_s$, $A_k$ represents the $k^{th}$ constituent phase with a size not greater than 10 microns, and $B_j$ represents the $j^{th}$ constituent phase with a size not less than 100 microns;

for the binary image of each constituent phase A, extracting five physical descriptors of the nearest neighbor distance d, number N, area S, aspect ratio α and volume fraction VF of all particles;

$$S_i = q_i (i = 1, 2, \ldots, N) \quad (1)$$

$$\alpha_i = \frac{a_i}{b_i} (i = 1, 2, \ldots, N) \quad (2)$$

wherein, $q_i$ represents an area of a pixel region occupied by the $i^{th}$ particle in the $k^{th}$ constituent phase, and $a_i$ and $b_i$ represent lengths of short axis and long axis of the $i^{th}$ particle in the $k^{th}$ constituent phase, respectively;

$$VF = \frac{\sum_{i=1}^{N} S_i}{M \times H} \quad (3)$$

wherein, M×H is an area of the original microscopic image $I_s$;

3) constructing a base image of the constituent phase B a) constructing a multi-resolution pyramid of the constituent phase $B_j$ constructing an L-layer multi-resolution pyramid of the binary images of the matrix phase and the constituent phase $B_1$ to obtain a sample pyramid image $X_j^l$ (l=1, 2, . . . , L) with a resolution from high to low, and constructing an L-layer pyramid $Y_j^l$ (l=1, 2, . . . , L) of $B_j'$ to-be-generated;

b) constructing a set of neighborhood pixels of the constituent phase $B_j$ for each pixel point t to-be-output, taking t point as a center, and expressing a neighborhood with a size of (2ω+1) as:

$$N_t = \{s : \|t-s\|_\infty \leq \omega, s \neq t\} \quad (4)$$

wherein, s represents the pixel points around the central pixel point t, and ω represents a size of the neighborhood;

searching pixel by pixel according to raster scanning order, and learning the neighborhood distribution in $X^{L-h}_j$ (h=1, 2 ..., L–1) and $Y^l_j$ (l=1, 2 ... L), an entire neighborhood set $N_P$ at this time comprising neighborhood pixels of the current layer $X^{L-k}_j$ and neighborhood pixels of the synthesized previous layer $Y^L_j$;

c) reconstructing the constituent phase $B_j$ according to texture synthesis according to the multi-resolution pyramid and the neighborhood pixels set in steps a) and b), gradually synthesizing a microscopic image $Y^L_j$ equivalent to $X^L_j$ from the lowest resolution level, and obtaining a final reconstructed image $Y^l_j$ by stacking resolution images layer-by-layer to the highest resolution layer, that is, the reconstructed result $B_j'$ of constituent phase $B_j$;

d) adjusting the composition of the constituent phase B repeating steps a) to c), superimposing the matrix phase with the reconstructed result of each constituent phase $B_j'$ to obtain the base image B' of all constituent phases B, identifying edges of all particles in B', and increasing or decreasing pixels at the edges of particles in the non-overlapping part, so as to ensure that the volume fraction of B' is consistent with that of the constituent phase B in the original microscopic image $I_s$;

4) constructing dispersion of the constituent phase $A_k$ on the synthesized base image B' of the constituent phase B, randomly generating centroid positions according to the number N of the $A_k$ particles extracted in step 2) to obtain an initialized microstructure, taking the centroid position distribution of the initialized microstructure and the particles in the sample $A_k$ binary image as the systems under high temperature and zero Kelvin respectively, setting initial parameters of the simulated annealing algorithm, randomly exchanging the centroid positions of particles, calculating a deviation between the nearest neighbor distance of the particles after exchange and the sample $A_k$ and a deviation between that before exchange and the sample $A_k$, if the deviation decreases, accepting the exchange, otherwise, calculating a probability of accepting an exchange according to the Metropolis rule:

$$P = \begin{cases} 1 & \Delta E \le 0 \\ e^{-\frac{\Delta E}{T(k)}} & \Delta E > 0 \end{cases} \quad (5)$$

wherein, T(k) represents a temperature of the current iteration step, and ΔE represents an energy change of the system;

gradually lowering the temperature and continuing to exchange centroid positions, terminating iteration until the deviation of the nearest neighbor distance d is less than 6, and obtaining the dispersion of the centroid of particles in the constituent phase $A_k$;

5) reconstructing the constituent phase $A_k$ according to the physical descriptors generating the shape and size of each cluster according to the area S and the aspect ratio α of all particles in the constituent phase $A_k$ extracted in step 2), and adding each cluster to the centroid position of the particles obtained in step 4) to obtain a reconstructed result $A_k'$ of $A_k$;

6) adjusting composition for the problem of pixel overlapping generated by a fusion of $A_k'$ and the base image B' of the constituent phase B, identifying the edges of all particles in the $A_k'$ and the base image B', and increasing or decreasing pixels at the edges of particles in a non-overlapping part until the volume fractions VF of the $A_k'$ and the base image B' are consistent with that of the constituent phase $A_k$ and all the constituent phases B in the sample image $I_s$;

7) repeating steps 4)-6) to reconstruct all the constituent phases A on the base image to obtain a final reconstructed image $I_c$ of $I_s$.

* * * * *